United States Patent
Mueller-Walz et al.

(10) Patent No.: US 10,471,077 B2
(45) Date of Patent: Nov. 12, 2019

(54) MEDICINAL AEROSOL FORMULATIONS

(71) Applicant: Jagotec AG, Muttenz (CH)

(72) Inventors: Rudi Mueller-Walz, Schopfheim (DE);
Lise-Marie Fueg, Arlesheim (CH)

(73) Assignee: Jagotec AG, Muttenz (CH)

( * ) Notice: Subject to any disclaimer, the term of this patent is extended or adjusted under 35 U.S.C. 154(b) by 0 days.

(21) Appl. No.: 15/265,467

(22) Filed: Sep. 14, 2016

(65) Prior Publication Data

US 2017/0189423 A1 Jul. 6, 2017

Related U.S. Application Data

(63) Continuation of application No. 14/279,751, filed on May 16, 2014, now abandoned, which is a continuation of application No. 13/503,245, filed as application No. PCT/EP2010/065573 on Oct. 15, 2010, now abandoned.

(30) Foreign Application Priority Data

Oct. 16, 2009 (GB) .................................. 0918149.6

(51) Int. Cl.
*A61K 31/58* (2006.01)
*A61K 47/10* (2017.01)
*A61K 31/137* (2006.01)
*A61K 47/22* (2006.01)
*A61K 9/12* (2006.01)
*A61K 31/56* (2006.01)
*A61K 9/00* (2006.01)
*A61K 31/167* (2006.01)
*A61K 45/06* (2006.01)

(52) U.S. Cl.
CPC .............. *A61K 31/58* (2013.01); *A61K 9/124* (2013.01); *A61K 31/137* (2013.01); *A61K 47/10* (2013.01); *A61K 47/22* (2013.01)

(58) Field of Classification Search
None
See application file for complete search history.

(56) References Cited

U.S. PATENT DOCUMENTS

| | | |
|---|---|---|
| 4,347,671 A | 9/1982 | Dias et al. |
| 5,476,603 A | 12/1995 | Buchwald et al. |
| 5,637,620 A | 6/1997 | Trofast et al. |
| 5,676,931 A | 10/1997 | Adjei et al. |
| 5,709,884 A | 1/1998 | Trofast et al. |
| 5,874,063 A | 2/1999 | Briggner et al. |
| 6,054,488 A | 4/2000 | Oliver et al. |
| 6,086,376 A | 7/2000 | Moussa et al. |
| 6,451,285 B2 | 9/2002 | Blondino et al. |
| 6,455,028 B1 | 9/2002 | Wulffhart et al. |
| 6,461,591 B1 | 10/2002 | Keller et al. |
| 6,475,467 B1 | 11/2002 | Keller et al. |
| 6,585,958 B1 | 7/2003 | Keller et al. |
| 6,743,413 B1 * | 6/2004 | Schultz ................ A61K 9/008 424/43 |
| 2002/0018753 A1 | 2/2002 | Blondino et al. |
| 2002/0025299 A1 | 2/2002 | Lewis et al. |
| 2002/0099023 A1 | 7/2002 | Boucher |
| 2002/0102294 A1 | 8/2002 | Bosch et al. |
| 2002/0103260 A1 | 8/2002 | Clarke et al. |
| 2003/0091512 A1 | 5/2003 | Adjei et al. |
| 2003/0114428 A1 | 6/2003 | Sequeira et al. |
| 2003/0223939 A1 | 12/2003 | Kordikowski et al. |
| 2004/0101483 A1 | 5/2004 | Muller-Walz et al. |
| 2004/0198708 A1 | 10/2004 | Kaplan et al. |
| 2005/0152846 A1 | 7/2005 | Davies et al. |
| 2006/0096522 A1 | 5/2006 | Singh |
| 2006/0257324 A1 | 11/2006 | Lewis et al. |
| 2007/0218011 A1 | 9/2007 | Mueller-Walz |
| 2007/0256685 A1 * | 11/2007 | Mueller-Walz ........ A61K 9/008 128/200.23 |
| 2012/0263766 A1 | 10/2012 | Mueller-Walz et al. |
| 2012/0282189 A1 | 11/2012 | Mueller-Walz et al. |
| 2014/0004052 A1 | 1/2014 | Mueller-Walz |
| 2014/0314684 A1 | 10/2014 | Mueller-Walz et al. |

FOREIGN PATENT DOCUMENTS

| | | |
|---|---|---|
| DE | 2503962 A1 | 8/1976 |
| EP | 0478456 A1 | 4/1992 |
| EP | 1325765 A1 | 7/2003 |
| GB | 2029441 A | 4/1924 |
| JP | 55361 B1 | 1/1980 |
| JP | 6135815 A | 5/1994 |

(Continued)

OTHER PUBLICATIONS

21 CFR Part 820 (16 pages); current as of Oct. 15, 2015; imported from parent '751 application Apr. 12, 2017.*
WHO Technical Report Series No. 929 (2005); Annex 4 (35 pages); imported from parent '751 application Apr. 12, 2017.*
Webb, Paul A.; "Volume and Density Determination for Particle Technologists"; Micrometrics Istrument Corp.; 16 pages; published Feb. 16, 2001.*
"1,1,1,2,3,3,3-Heptafluoropropane." Wikipedia. Web. Jul. 19, 2013. http://en.wikipedia.org/wiki/1,1,1,2,3,3,3-Heptafluoropropane.
"Cromolyn Sodium." PubChem. Web. Jul. 19, 2013. http://pubchem.ncbi.nlm.nih.gov/summary/summary.cgi?cid=2882.
"Formoterol Fumarate Dihydrate." Pharmeuropa. 14.4(2002):693-696.
Bowen et al. "Particle Size Distribution Measurement From Millimeters to Nanomaters and From Rods to Platelets." J. Disp. Sci. Technol. 23.5(2002):631-662.
Crowder et al. "2001: An Odyssey in Inhaler Formulation and Design." Pharm. Technol. 25(2001):99-113.
Postma et al. "Treatment of Asthma by the Inhaled Corticosteroid Ciclesonide Given Either in the Morning or Evening." Eur. Respir. J. 17.6(2001):1083-1088.

(Continued)

Primary Examiner — Jeffrey T. Palenik
(74) Attorney, Agent, or Firm — Muriel Liberto, Esq.; Mintz Levin Cohn Ferris Glovsky and Popeo, P.C.

(57) ABSTRACT

The present invention provides a medical aerosol suspension formulation of MDI administration, comprising: a) micronized pa-agonist; b) micronized corticosteroid; c) a sibtherapextric quantity of a moisture-scavenger excipient; and d) a HFA propellant; wherein (a), (b), and (c) and their respective relative amounts are selected such that they associate to form floccules having a density substantially the same as that of the HFA propellant.

13 Claims, 2 Drawing Sheets

(56) References Cited

FOREIGN PATENT DOCUMENTS

| | | |
|---|---|---|
| JP | 9077605 A | 3/1997 |
| WO | WO-9218110 A1 | 10/1992 |
| WO | WO-9505805 A1 | 3/1995 |
| WO | WO-9515151 A1 | 6/1995 |
| WO | WO-9833479 A1 | 8/1998 |
| WO | WO-9834595 A1 | 8/1998 |
| WO | WO-9851825 A1 | 11/1998 |
| WO | WO-0006121 A1 | 2/2000 |
| WO | WO-0007567 A1 | 2/2000 |
| WO | WO-0028979 A1 | 5/2000 |
| WO | WO-0047203 A1 | 8/2000 |
| WO | WO-0048587 A1 | 8/2000 |
| WO | WO-0189491 A1 | 11/2001 |
| WO | WO-0189492 A1 | 11/2001 |
| WO | WO-0207672 A2 | 1/2002 |
| WO | WO-02030394 A2 | 4/2002 |
| WO | WO-02078671 A1 | 10/2002 |
| WO | WO-03074024 A1 | 9/2003 |
| WO | WO-03/088945 A1 | 10/2003 |
| WO | WO-03086349 A1 | 10/2003 |
| WO | WO-04019985 A1 | 3/2004 |
| WO | WO-05004927 A2 | 1/2005 |
| WO | WO-05027878 A1 | 3/2005 |
| WO | WO-05034911 A1 | 4/2005 |
| WO | WO-05034927 A2 | 4/2005 |
| WO | WO-2006/040598 A2 | 4/2006 |
| WO | WO-2006/040598 A3 | 4/2006 |
| WO | WO-07121913 A2 | 11/2007 |
| WO | WO-11045429 A1 | 4/2011 |
| WO | WO-11045432 A1 | 4/2011 |

OTHER PUBLICATIONS

Doucet et al. (2005). WHO Tech Report Series, No. 929, 35 pages.
Electronic Code of Federal Regulations, 21 CFR 820.250 weblink: (www.ecfr.gov/cgi-bin/text-idx?SIDS= bac2dd3d9572c78d4157aec7fc3d2c05&mc=true&node=pt21.8.820 &rgn=div5#se21.8.820_1250); downloaded Oct. 19, 2015. 16 pages.
IUPAC Compendium of Chemical Technology 2014 (the Gold Book), 'Agglomeration' http://goldbook.iupac.org, last visited Aug. 5, 2016, 1 page.
Notice of Opposition dated Sep. 24, 2015, for European Application No. 10768922.6, 27 pages.

\* cited by examiner

MEDICINAL AEROSOL FORMULATIONS

CROSS REFERENCE TO RELATED APPLICATIONS

This application is a continuation of U.S. patent application Ser. No. 14/279,751, filed on May 16, 2014, which is a continuation of U.S. patent application Ser. No. 13/503,245, filed Jul. 24, 2012, which is a U.S. National Stage Application, filed under 36 U.S.C. § 371, of Application No. PCT/EP2010/065573, filed on Oct. 15, 2010 and claims priority to, each of which is incorporated herein in its entirety.

The present invention relates to medicinal aerosol formulations for use with pressurised metered dose inhalers (abbreviated pMDI or MDI), and especially improved medicinal aerosol formulations suitable for aerosol administration.

Drugs for the treatment of respiratory diseases and disorders, such as $\beta_2$-agonists and anti-cholinergics, corticosteroids, anti-allergies, and others, are frequently administered directly to the lungs via inhalation. Administration via inhalation can increase the therapeutic index and reduce side effects of the drugs compared to administration by other routes, such as orally or intravenously. Administration by inhalation can be in the form of either dry powders or aerosol formulations which are inhaled by the patient either through use of an inhalation device or as a spray.

MDIs are known devices for the administration of aerosol medicinal formulations to the respiratory tract through inhalation by the patient. The term MDI is used to describe a metered dose inhaler, of which a standard unit comprises a canister filled with the medicinal formulation, a drug metering valve and a mouthpiece. The MDI may be selectively activated by the user to deliver successive individual doses of drug by actuation of the metering valve, such that an accurately metered dose of the formulation is expelled via the actuator mouthpiece for delivery into the patient's respiratory tract.

MDI formulations are an advantageous delivery method for many reasons, including that they deliver the drug instantaneously and do not rely on the inhalation capacity of the user. This is particularly important when considering the type of condition to be treated with the drug, such as an asthma attack. Since MDI devices usually contain a sufficient amount of the medicinal formulation for multiple unit doses, it is important that the formulation is such that it may be successfully and repeatedly used with a MDI device. The formulation must be delivered in a reliable manner and in the correctly calculated dose. The formulation must also comply with the requirements for pharmaceutical quality, stability and robustness set out by regulatory bodies.

MDIs typically use a propellant to expel droplets or particles of the formulation as an aerosol, containing the drug, to the respiratory tract.

For a long time the propellant gases used were fluorochlorohydrocarbons which are commonly called Freons or CFCs, such as $CCl_3F$ (Freon 11 or CFC-11), $CCl_2F_2$ (Freon 12 of CFC-12), and $CClF_2$—$CClF_2$ (Freon 114 of CFC-114). However it has been discovered that these CFC propellants are particularly harmful to the environment and their production and, at the time of writing, their use in medicinal formulations is being phased out. An alternative propellant was therefore sought which was safe to use with inhalation drugs.

Hydrofluoroalkanes (HFAs), also known as hydro-fluorocarbons (HFCs), have been proposed as alternative propellant gases, because they contain no chlorine and are considered to be less destructive to the atmosphere. In particular 1,1,1,2-tetrafluoroethane (HFA 134a) and 1,1,1,2,3,3,3-heptafluoropropane (HFA 227) have been found to be good replacement propellants for the CFC propellants and a number of medicinal aerosol formulations using these propellants have been proposed.

Formulations administered via MDIs can be in the form of solutions or suspensions. In suspension formulations the drug is manufactured as a fine particle powder which is then suspended in a liquefied propellant or propellant blend. The suspension formulation can be stored in a sealed canister with sufficient pressure to maintain the propellant in liquid form. For example, the vapour pressure for a HFA227 formulation may typically be around 1.96 bar at 0° C., 3.90 bar at 20° C. and 7.03 bar at 40° C. In solution formulations the drug is solubilised in the liquefied propellant phase. When the metering valve is actuated, a dose is delivered in rapidly deployed fine droplets.

Suspension formulations are usually preferred because of generally improved chemical stability of the suspended particles in comparison to solubilised drugs. Stability problems associated with the chemical degradation of solubilised drug compounds are known in the art.

In order that a medicinal formulation is suitable for use with an MDI device, the particle size of the deployed aerosol must be small enough that it can be inhaled into the lungs of the users, be that a grown adult, child or elderly/infirm person. Therefore, the particles of the suspension formulation need to be microfine with a mean aerodynamic particle diameter (measured as Mass Median Aerodynamic Diameter (MMAD)) of about 1 to 10 μm, and preferably 1 to 6 μm. Micronised particles of this size can be obtained by various methods known in the art, for example mechanical grinding or spray drying.

The amount of active drug deployed in fine, inhalable particles is called the fine particle dose (FPD) or the fine particle fraction (FPF), which is defined as the percentage of the fine particle dose relative to the total amount of released active compound. Both are determined by the measurement of the aerodynamic particle size distribution with a cascade impactor or liquid impingers. These are routine tests for which the methods and apparatus are described in the pharmacopeias. For example, formulations of the present invention meet the requirement set out in Chapter <601> of the United States Pharmacopeia (USP) 32 or in the inhalants monograph 2.9.18 of the European Pharmacopeia (Ph.Eur.), $6^{th}$ edition 2009.

Microfine particles for use in suspension formulations do, however, have some associated drawbacks. They have a large surface area and therefore an unfavourable ratio of surface area to volume or mass. This ratio results in strong interaction forces between the particles and undesirable powder cohesion and adhesion tendencies. This in turn can lead to difficult handling due to poor flow rate of the powdered drug during manufacture and poor suspension properties of the MDI formulation. Such powders are therefore difficult to formulate for use with a MDI device, difficult to handle and are strongly influenced by electrostatic charge, processing methods, humidity, etc.

Formoterol fumarate dihydrate (hereafter called formoterol) is a long acting $\beta_2$-agonist bronchodilator ($\beta$-sympathomimetic) commonly used for the relief of asthma symptoms. Fluticasone propionate (hereafter called fluticasone) is a potent synthetic corticosteroid which is also often prescribed as a treatment for asthma, chronic obstructive pulmonary disease and allergic rhinitis. Both are examples of drugs which can be individually delivered via a MIN product.

Formoterol and fluticasone (but in particular formoterol) are each notoriously difficult compounds to be formulated for use with MDIs. One reason for this is because the potency of these drugs means that only a very small dose should be delivered in each case and the concentration of the drug within the HFA formulation is therefore very low. This exacerbates the problems highlighted above with regard to the manufacture of the aerosol formulation and the pharmaceutical quality, stability and robustness of the aerosol formulation, as required by the regulatory authorities, can therefore be compromised. Robustness of the formulation may be determined when handled by the patient, under different conditions of use, upon prolonged storage or upon storage under stress conditions (e.g. freeze-thaw cycles). Due to the low concentration of drug present within the formulation, fluctuations in the local homogeneity of the drug suspended in the propellant (i.e., in a volume range of about 50 µL) can result in deviation in the delivered dose.

It has also been shown that MDI formulations comprising hydrofluoroalkanes (UFAs) as propellants are difficult to formulate because there are only a limited number of currently known suspension aids that are regarded as safe for inhalation, which can be employed to reduce undesirable particle cohesion and adhesion tendencies and to improve the physical stability of the suspension formulation using such HFA propellants.

Furthermore, chemical stability of the HFA formulations is particularly a problem when bronchodilator $\beta_2$-agonists, such as formoterol, are used owing to their susceptibility to oxidative and hydrolytic conditions. Hydrolysis is one of the major identified factors affecting degradation of formoterol under stress conditions (e.g. 40° C./75% relative humidity) because such formulations are usually sensitive to moisture and are susceptible to the ingress of moisture from the surrounding air.

Slight concentration changes or changes in the physical stability of the MDI suspension which may occur during storage due to temperature changes and/or moisture ingression may lead to significant differences in the metered and delivered doses (e.g. dose uniformity failures). These differences may also be seen as a reduction in the inhalable proportion of the released dose, which is determined in vitro as the FDP or FPF.

This reduction may be caused by strong adsorption of drug particles to internal surfaces of the container closure system (canister and metering valve) and by agglomeration of microfine particles as a result of imperfect suspension stability. It is found that water molecules, which may accumulate in the MDI formulation during long term storage and use, are particularly detrimental to the suspension since they interact with the polar drug particles and result in a stronger binding between the particles.

In view of the above described problems, it is generally thought to be key to prevent ingression of water to reduce hydrolysis of formoterol formulations.

Cromolyn sodium (DSCG) is an excellent internal moisture scavenger and a suspension enabler. It has been used for administration via the inhalation route and has been demonstrated to be clinically safe. However, it has been shown that cromolyn sodium itself has a biological pharmacological effect and so its use in the HFA formulations described above has previously been avoided so that an effect over and above that of the fluticasone and formoterol is not seen.

The type of propellant used also has an effect on the actuation of the metered dose inhaler. The use of HFA propellants instead of CFC propellants has led to a further problem with the fine particles of suspended drug. This is because the HFA propellants have a higher polarity than the CFC propellants previously used, which causes the HFA suspension formulations to be comparatively more susceptible to physical stability problems. When active agents are used that have a density lower than that of the liquid in which they are placed then they have a tendency to float and cream which can lead to an irregularity in the dosage delivered. The drugs also frequently adhere to the inside surface of the device and the dosage mechanism.

This deposition on the walls of the metering valve has been found to be significantly increased compared to the CFC propellant. This deposition can lead to a reduction in the actual dose dispensed. This adherence can also lead to the device failing owing to a clogging of the internal mechanisms of the canister or blockage of the metering valve.

Previously proposed devices have used a container in which the interior surfaces are coated with fluorocarbon polymer plastics; see WO-A-96/32150 and U.S. Pat. No. 6,596,260. However, the problems with such systems include that the fluorocarbon polymers, and their constituents, can be soluble in the propellants used in the aerosol formulations. Also such coatings themselves need to undergo safety tests and product formulation development in order to give a safe and stable product. These tests further add to the production cost which adds to the overall cost of the product.

Coating the internal surfaces of the containers to prevent adsorption also causes problems with regard to the use of certain metals for the canister. The most commonly used metals for the canister are aluminium alloys. The plastics coating must undergo heat treatment in order to be cured which results in the strength of the container being compromised because the metal canister layer becomes softer and malleable from the heat.

The plastics coating material itself can also lead to contamination of the medicinal formulation because there is the potential for leachable compounds to find their way into the formulation contained within the canister. Such leachable compounds can lead to degradation of the drug compound within the medicinal formulation and a less effective and less robust product. The shelf-life of the product may also be compromised with degradation of the active ingredients upon storage.

There are, therefore, a number of important parameters that need to be considered when producing a medicinal aerosol formulation for use with a MIN.

Some of the difficulties in formulating fluticasone propionate and formoterol fumarate within a single formulation have been addressed in WO 2005/034911 by the introduction of a drying step to dry the formoterol fumarate prior to mixing it together with the other ingredients. However, the problems associated with long term storage of such formulations have not been addressed.

The present application seeks to alleviate at least some of the aforementioned problems with the prior art.

Accordingly, a first aspect of the present invention is directed to a medicinal aerosol suspension formulation for MDI administration, comprising (a) a micronised $\beta_2$-agonist, (b) a micronised corticosteroid, (c) a sub-therapeutic quantity of a moisture-scavenger excipient, and (d) a HFA propellant wherein (a), (b) and (c) and their respective relative amounts are selected such that they associate to form floccules having a density substantially the same as that of the HFA propellant.

It has been found that the constituents of the present formulation tend to associate in such a way as to form floccules (also known as flocs, flocculi or flocculates). Floccules comprise a loosely held mass or aggregation of discrete fine particles held together in a network-like fragile structure, suspended in solution. The aggregates formed by the floccules tend to break up easily under the application of small amounts of sheer stress, such as gentle agitation of the canister, and reform an extended network of particles after the force is removed. Flocculation, therefore, imparts a structure to the suspension with virtually no increase in viscosity. In contrast to deflocculated systems, the floccules will settle rapidly, usually to a high sediment volume and may be easily re-suspended even after standing for prolonged periods of storage, for example after 3, 6, 9 or 12, 18 months or longer.

It has been found that, once associated, the floccules of the present formulation have a density to match that of the density of the propellant in which they are placed. This gives the floccules the ability to remain in suspension without the tendency to cream, float or sink. The suspension formulation of the present invention may therefore remain in a viable formulation for an extended period of time and results in a robust product with an extended shelf life and improved reliability of the end product.

Furthermore, the tendency to form these floccules may provide enhanced uniformity in the suspension and less fluctuation in the local homogeneity which then results in a product which may have reduced deviation in the delivered dose.

In addition to the above, the floccules afford an increased stability to the suspension formulation. This increased stability of the suspension means that the ingredients associate together in preference to associating with the internal surfaces of the canister or metering valve of the inhaler. Therefore there is a reduced tendency to adhere to the inside of the container or the metering valve of the canister through which the suspension formulation must pass. This may lead to an increase in the reliability of the delivered dose. In addition there are fewer tendencies to block the actuation mechanism and the metering valve, which in turn provides for a formulation which can be reliably and repeatedly dispensed at the correct amount.

Typically, suspension formulations, especially MDI suspension formulations using HFA propellants are inherently physically unstable. The formulations form two phases, a liquid propellant phase and a suspended particulate phase, which segregate as a result of gravitational force. Within the canister, areas having different concentrations of suspended particles may also exist as a result of small temperature fluctuations inside the canister which leads to thermal motion of particles. However, the tendency of formulations according to the present invention to associate to form floccules results in all the active ingredients remaining associated right up until the moment they are dispensed from the MDI and enter the patient's respiratory system. This provides for a formulation with an improved quality and improved ability to adhere to a calculated dose.

Preferably the HFA propellant is HFA 227, HFA 227 is an inert propellant with low toxicity and is suitable for use in metered-dose inhalers. HFA 227 propellant, when combined with a small amount of ethanol to form the liquid propellant phase has a calculated density, over a range of temperatures, as follows:

| Temp. | Calculated density of [g/ml] |
|---|---|
| 10° C. | 1.45 |
| 15° C. | 1.43 |
| 20° C. | 1.41 |
| 22° C. | 1.40 |
| 25° C. | 1.39 |
| 30° C. | 1.36 |

The above numbers were calculated using thermodynamic laws on ideal mixtures. However, in practice the liquid mixtures are likely to behave as non-ideal mixtures and the "true" densities may be slightly different to the calculated values.

It is therefore advantageous to have a formulation wherein the average density of the floccules (comprising the micronised $\beta_2$-agonist, micronised corticosteroid and moisture-scavenger excipient) is substantially the same as the density of the propellant ±0.2 g/cm$^3$, preferably ±0.1 gcm$^3$, more preferably ±0.05 g/cm$^3$ of the propellant.

The average density of the floccules may be calculated using any standard technique, for example by determining the true particle density of each solid component by helium pycnometry. The density of the floccules may therefore substantially match that of the density of the propellant over a range of temperatures of 10° C. to 30° C. under which a MDI would usually be operated by a user.

Preferably the corticosteroid is fluticasone propionate or a pharmaceutically acceptable salt thereof. The corticosteroid is advantageously present in an amount of 0.01-0.6% by weight; preferably between 0.02-0.5% by weight; and more preferably 0.03-0.4% by weight, based on the total weight of the formulation. This is the advantageous amount in order to be effective in use and also to form the correct density of floccules for suspension in the propellant.

The corticosteroid preferably has a defined particle size of less than 10 μm for 100%, less than 6 μm for 90%, less than 3 μm for 50%, and less than 2 μm for 10% of the particles.

Preferably the $\beta_2$-agonist is formoterol fumarate dihydrate or a pharmaceutically acceptable salt or derivative thereof. The $\beta_2$-agonist is preferably present in an amount of 0.003-0.04% by weight; preferably 0.004-0.03% by weight; and more preferably 0.005-0.02% by weight, based on the total weight of the formulation. In a preferred embodiment, formoterol fumarate dihydrate may be employed in an amount of 0.003-0.008% by weight, based on the total weight of the formulation. In an alternative preferred embodiment, formoterol fumarate dihydrate may be employed in an amount of 0.01-0.04% by weight, based on the total weight of the formulation. As with the corticosteroid, this is the advantageous amount of $\beta_2$-agonist in order to be able to be effective in use and also to form the correct density of floccules for suspension in the propellant.

The $\beta_2$-agonist preferably has a defined particle size of less than 10 μm for 100%, less than 6 μm for 90%, less than 3 μm for 50%, and less than 2 μm for 10% of the particles.

Preferably, the moisture scavenger excipient is sodium cromolyn (DSCG) and is advantageously present at sub-therapeutic levels such that it does not exert a biological effect itself and is pharmaceutically inactive. The moisture scavenger is therefore suitably present in an amount of 0.01-0.1% by weight; preferably 0.016-0.09% by weight; more preferably 0.02-0.08% by weight; more preferably 0.025-0.07% by weight; more preferably 0.03-0.05% by weight; more preferably 0.03-0.04% by weight, based on the total weight of the formulation.

The moisture scavenger preferably has a defined particle size of less than 10 μm for 100%, less than 6 μm for 90%, less than 3 μm for 50%, and less than 2 μm for 10% of the particles.

It has been found that DSCG is an excellent suspension enabling agent when used in formulations including a HFA propellant. DSCG itself consists of particles which encourage and allow the formation of heterogeneous floccules with the active agents.

DSCG acts to aid stabilisation of the formulation, particularly against hydrolysis by competitive water absorption. DSCG exists as a single crystal form that is non-stoichiometric with regard to water content and adsorbs or desorbs water rapidly in response to changes in relative humidity. DSCG crystals are universal in the extent of reversible water absorption without collapse of the crystal lattice and can absorb up to 9 molecules of water per mol, which is about 24% w/w. The crystal structure analysis by X-ray diffraction reveals the existence of channels that are capable of reversibly accommodating a variable number of water molecules (depending on the ambient relative humidity) with only small dimensional changes within the lattice. Despite its large moisture adsorption capacity DSCG is not deliquescent (like, for example, sodium sulphate) but is solid in the range of 10 to 90% r.h.

In the present invention DSCG acts to stabilize the fine particle fraction (FPF) in the formulation by competitively binding free (i.e. molecular dissolved) water present within the propellant phase. This assists in stabilising the fine particle fraction by preventing agglomeration of suspended particles (i.e. formation of liquid and/or crystal bridges) and particle growth (i.e. Ostwald ripening) on stability. This allows for a more robust product during storage and use as the formulation has improved tolerance to the presence of internal water. For example, up to 600 ppm of total internal water may be tolerated. Furthermore this allows for a much longer 'use period' once the product is in the patients hands. In addition, there is a reduced tendency to adhere to surfaces, which allows the medicinal formulation to be used with an uncoated canister instead of a canister which has its internal surfaces coated with a polymer.

Preferably the medicinal aerosol suspension formulation further comprises a wetting agent; more preferably the wetting agent is a dehydrated alcohol; and most preferably the wetting agent is ethanol which may be present in an amount of 0.01-3% by weight; preferably 0.05-2.5% by weight; and more preferably 1.0-2.0% by weight, based on the total weight of the formulation.

A wetting agent facilitates the wetting of the active agents within the liquefied propellant and thus the suspension manufacture such that the active agents do not become partially solubilised. The addition of such agents requires a delicate balancing act between allowing the active agents to become wetted without being partially solubilised and causing them to be partially solubilised such that Ostwald ripening, particle growth and, eventually, stability failures occur.

Ethanol can be added in small quantities as it also helps to prevent the deposition of the active agents on the walls of the canisters and mechanical parts.

In a preferred form, the formulation of the present invention therefore comprises as pharmaceutically active ingredients formoterol and fluticasone and as pharmaceutically inactive ingredients sodium cromolyn, HFA 227 and ethanol.

A further aspect of the present invention is directed to a pharmaceutical composition comprising, 0.01-0.6% by weight of micronised corticosteroid; 0.003-0.04% by weight of micronised $\beta_2$-agonist; and 0.01-0.1% by weight of sodium cromolyn.

Preferably the corticosteroid is micronised fluticasone propionate.

Advantageously the $\beta_2$-agonist is micronised formoterol fumarate dihydrate.

Preferably the pharmaceutical composition further comprises a wetting agent, more preferably the wetting agent is a dehydrated alcohol, most preferably ethanol. Preferably the wetting agent is present in an amount of 0.01-3% by weight; preferably 0.05-2.5% by weight; and more preferably 1.0-2.0% by weight, based on the total weight of the formulation.

A further aspect of the present invention is directed to a pharmaceutical suspension formulation comprising about 0.003-0.04% formoterol fumarate dihydrate, about 0.01-0.06% fluticasone propionate, about 0.01-0.1% suspension agent and about 0.01-3% dehydrated alcohol.

Preferably the suspension agent is sodium cromolyn (DCSG) which also allows the active agents to remain in the suspension state for a prolonged period of time. This improves the shelf-life of the product as it can be effective for a longer time after production.

Furthermore, DECO acts as a 'bulking agent', since its use increases the concentration of particles suspended in the formulation, therefore minimising inherent concentration changes in the suspension without the need for the addition of other excipients. DSCG also provides the usual benefits of bulking agents, namely affording the preparation of a more homogeneous suspension, which leads to improved accuracy of the dose.

A further aspect of the present invention is directed to a product containing formoterol fumarate dihydrate, fluticasone propionate and sodium cromolyn as a combined preparation for separate, sequential or simultaneous use in the treatment of inflammation and preferably for the treatment of asthma and allergic rhinitis.

A further aspect of the present invention is directed to the use of sodium cromolyn in the preparation of a pharmaceutical suspension formulation in HFA propellant comprising fluticasone propionate and formoterol fumarate dihydrate microparticles for forming floccules of fluticasone propionate, formoterol fumarate dihydrate and sodium cromolyn having a density substantially the same as that of the HFA propellant.

According to a further aspect of the present invention, there is provided the use of 0.01 to 0.1% sodium cromolyn in the preparation of a pharmaceutical suspension formulation in HFA propellant comprising 0.01 to 0.6% fluticasone propionate and 0.003 to 0.04% of formoterol fumarate dihydrate microparticles for forming floccules of fluticasone propionate, formoterol fumarate dihydrate and sodium cromolyn having a density substantially the same as that of the HFA propellant.

Preferably, the average density of the floccules is substantially the same as the density of the HFA propellant ±0.2 g/cm$^3$, preferably ±0.1 gcm$^3$, more preferably ±0.05 g/cm$^3$ of the propellant.

Preferably, the pharmaceutical suspension formulation additionally comprises a wetting agent, preferably a dehydrated alcohol, preferably ethanol.

According to a further aspect of the present invention, there is provided a method of increasing the stability of a medicinal aerosol suspension formulation of a micronised $\beta_2$-agonist and a micronised corticosteroid in HFA propellant over a prolonged period of storage, comprising the addition of a sub-therapeutic amount of sodium cromoglycate, wherein the respective relative amounts of the micronised $\beta_2$-agonist, micronised corticosteroid and sodium cromoglycate are selected such that they associate to form floccules having a density substantially the same as that of the HFA propellant.

Preferably the prolonged storage is for 3, 6, 9, 12 or 18 months. Preferably the water content of the suspension formulation after prolonged storage is in the range of 500 ppm to 800 ppm, preferably 600 ppm to 700 ppm.

Examples of suitable dosage strengths of a pharmaceutical composition in accordance with the present invention may be found in the following table.

TABLE 1

Composition of examples of dosage strengths of the formulation % w/w.

|  | Flutiform 25/5 | Flutiform 50/5 | Flutiform 125/5 | Flutiform 250/5 |
|---|---|---|---|---|
| Nominal dose | 50 mcg FP and 10 mcg FF | 100 mcg FP and 10 mcg FF | 250 mcg FP and 10 mcg FF | 500 mcg FP and 10 mcg FF |
| Fluticasone | 0.0357 | 0.0714 | 0.1785 | 0.3570 |
| Formoterol | 0.0071 | 0.0071 | 0.0071 | 0.0071 |
| Cromolyn sodium | 0.0343 | 0.0343 | 0.0343 | 0.0343 |
| Ethanol | 1.43 | 1.43 | 1.43 | 1.43 |
| HFA 227 | qs ad 100.0 | qs ad 100.0 | qs ad 100.0 | qs ad 100.0 |

|  | Flutiform 250/10 | Flutiform 250/10 |
|---|---|---|
| Nominal dose | 500 mcg FP and 20 mcg FF | 500 mcg FP and 20 mcg FF |
| Fluticasone | 0.3570 | 0.3570 |
| Formoterol | 0.0142 | 0.0142 |
| Cromolyn sodium | 0.0343 | 0.0686 |
| Ethanol | 1.43 | 1.43 |
| HFA 227 | qs ad 100.0 | qs ad 100.0 |

Following is a description by way of example only with reference to the accompanying drawings of embodiments of the present invention.

EXAMPLES

Example 1

The following compositions shown below in Table 2 were made up and the density of the floccules of fluticasone, formoterol and cromolyn sodium were calculated and compared to the calculated density of the liquid phase (comprising 1.43% w/w of anhydrous ethanol and HFA 227) over a range of temperatures.

TABLE 2

Compositions of pharmaceutical formulations.

|  | Flutiform 25/5 | Flutiform 50/5 | Flutiform 125/5 | Flutiform 250/5 | Flutiform 250/10 |
|---|---|---|---|---|---|
| Nominal dose | 50 mcg FP and 10 mcg FF | 100 mcg FP and 10 mcg FF | 250 mcg FP and 10 mcg FF | 500 mcg FP and 10 mcg FF | 500 mcg FP and 20 mcg FF |
| Fluticasone | 0.0357 | 0.0714 | 0.1785 | 0.3570 | 0.3570 |
| Formoterol | 0.0071 | 0.0071 | 0.0071 | 0.0071 | 0.0142 |
| Cromolyn sodium | 0.0343 | 0.0343 | 0.0343 | 0.0343 | 0.0343 |
| Ethanol | 1.43 | 1.43 | 1.43 | 1.43 | 1.43 |
| HFA 227 | qs ad 100.0 | qs ad 100.0 | qs ad 100.0 | qs ad 100.0 | qs ad 100.0 |

The density of the liquid phase was determined based on the thermodynamic laws on ideal mixtures. However, in practice the liquid mixtures are likely to behave as non-ideal mixtures and the "true" densities may be slightly different to the calculated values.

The average density of the floccules was determined by measuring the true particle density of each solid component by helium pycometry.

The results of the density calculations are shown in Tables 3 and 4.

TABLE 3

Calculated density of liquid phase.

| Temp. | Calculated density of liquid phase [g/ml] |
|---|---|
| 10° C. | 1.45 |
| 15° C. | 1.43 |
| 20° C. | 1.41 |
| 22° C. | 1.40 |
| 25° C. | 1.39 |
| 30° C. | 1.36 |

TABLE 4

Calculated density of floccules

| Composition | Calculated density of floccules (g/ml) |
|---|---|
| Fluticasone/formoterol 25/5 (25 μg fluticasone and 5 μg of formoterol per actuation) | 1.47 |
| Fluticasone/formoterol 50/5 | 1.43 |
| Fluticasone/formoterol 125/5 | 1.40 |
| Fluticasone/formoterol 250/5 | 1.38 |
| Fluticasone/formoterol 250/10 | 1.38 |

It can be seen from the above results in Tables 3 and 4 that the average density of the floccules substantially matches the calculated density of the liquid phase within ±0.2 g/ml.

Example 2

The batches shown in Table 5 were made up and tested (over a range of 'use temperatures' from 10 to 30 degrees Celsius):

TABLE 5

Composition of Batch 1 and Batch 2.

| | Description | | | |
|---|---|---|---|---|
| | Batch 1 Fluticasone/formoterol formulation (nominal dose 100 μg fluticasone/ 10 μg formoterol) | | Batch 2 Fluticasone/formoterol formulation without DSCG (for comparison, not part of the present invention) | |
| Composition | % w/w | g | % w/w | g |
| Fluticasone propionate | 0.0714 | 2.340 | 0.0714 | 2.340 |
| Formoterol fumarate dihydrate | 0.0071 | 0.234 | 0.0071 | 0.234 |
| Cromolyn sodium (DSCG) | 0.0343 | 1.123 | 0.0000 | 0.000 |
| Ethanol | 1.43 | 46.8 | 1.43 | 46.8 |
| HFA 227 | qs to 100.0 | 3225.5 | qs to 100.0 | 3226.6 |

The size of each batch was 3.3 kg (approximately 300 units). Ethanol 96.5% w/w (97.75% v/v) was used to challenge the formulation with a water level which was about similar to the amount contained in the formulation at the end of the envisaged shelf-life. The water content of all raw materials except HFA 227 was determined by Karl-Fischer analysis prior to preparation of the suspension.

The appropriate amounts of the micronised active substances were weighed and transferred into the batching vessel. The appropriate amount of sodium cromolyn, (DSCG) was added and the vessel closed. The propellant mixture of HFA 227 (apaflurane) with 1.45% alcohol was made in a separate vessel and transferred into the batching vessel. The solid materials were dispersed in the liquefied propellant by use of a rotor-stator homogenizer at 2900 rpm for 30 min. The homogeneous bulk suspension was cooled to 4° C. and re-circulated between the vessel and the Pamasol aerosol filling machine P2001.

Pharmaceutical aerosol canisters with 14 ml brimful volume were crimped with 50 mcl metering valves using a Pamasol P2005 crimping machine. Aliquots of 11±0.5 g suspension were filled into the crimped canisters by the P2001 filling machine. The weight of each filled canister was checked; all filled canisters were subjected to a heat stress test at 56° C. and stored one month prior to assembly with the actuator for testing.

Figure 2:
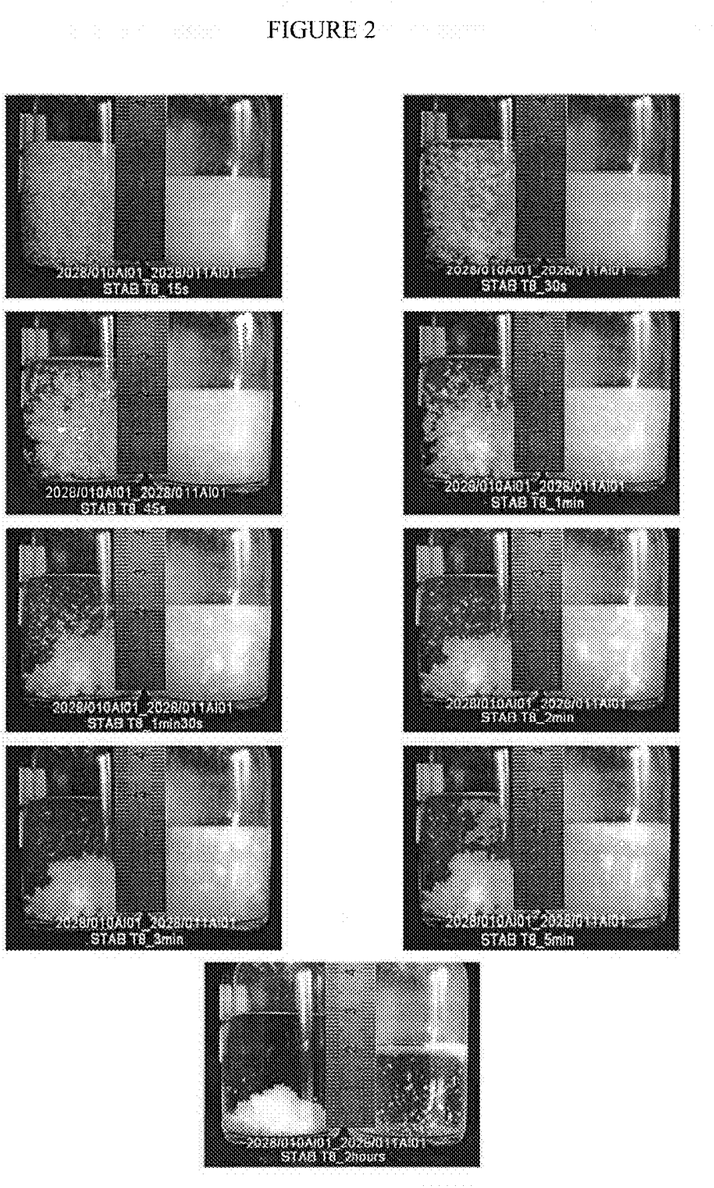
FIG. 2—Photographs of Suspension in Glass Vials at Different Time Points after Shaking.

Glass vials were filled in addition to the above canisters with the fluticasone/formoterol formulations of Batch 1 and Batch 2 HFA-MDI to assess suspension stability visually and by time lapse photography, see FIG. 2. The glass vials were shaken and photographs were taken 15 seconds, 30 seconds, 45 seconds, 1 minute, 1 minute 30 seconds, 2 minutes, 3 minutes, 5 minutes and 2 hours after this agitation.

The following analytical tests were performed in relation to Batch 1 and 2:

TABLE 6

Tests performed.

Figure 1:
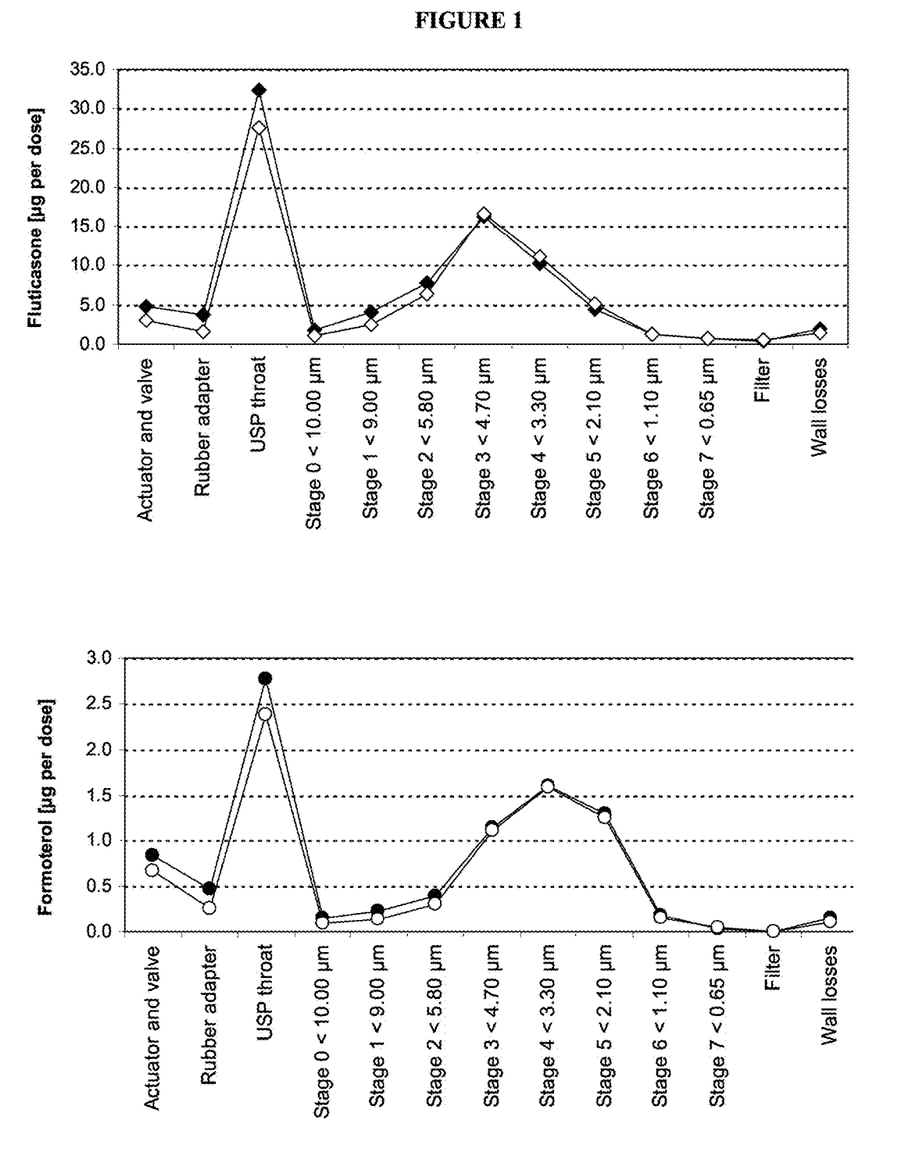
FIG. 1—Aerodynamic particle size distribution for fluticasone and formoterol.

| Description | Method | Table in which results are displayed. |
|---|---|---|
| Drug content (assay) | HPLC | Table 7 |
| Dose content uniformity (inter-inhaler) | HPLC | Table 8 |
| Dose content uniformity through canister life (intra-inhaler) | HPLC | Table 9 |
| Particle size distribution (by Andersen cascade impactor) | HPLC | FIG. 1 |
| Water content | Karl Fischer | Table 7 |
| Interaction between content and container (canister and valve) | HPLC | Table 10 |
| Suspension stability (in filled glass vials) | Time lapse photography | FIG. 2 |

TABLE 7

Drug, DSCG and water content of Fluticasone/formoterol formulation 100/10 Batches 1 (Fluticasone/formoterol formulation 100/10 with DSCG) and 2 (without DSCG) upon release from the MDI.

| | Batch No. | |
|---|---|---|
| | 1 | 2 |
| Mean fluticasone content [μg per g suspension/% of target] (RSD %, n = 3) | 679.0/95.1% (0.4%) | 658.0/92.2% (4.6%) |
| Mean formoterol content [μg per g suspension/% of target] (RSD %, n = 3) | 68.2/95.5% (0.4%) | 64.7/90.6% (5.3%) |
| Mean DSCG content [μg per g suspension/% of target] (RSD %, n = 3) | 321.0/93.7% (0.3%) | N.A. |
| Mean water content [ppm] (RSD %, n = 3) | 672 (12.6%) | 624 (5.1%) |

Table 7 shows the water content of the batches when ethanol 96.5% w/w was included in the formulation, thereby adding 500 ppm to the formulation in addition to the moisture typically present due to the manufacture process itself. The slightly higher value for Batch 1 may have been due to the presence of DCSG. The water level found in the two batches is that as would typically be expected after long-term storage of the product or after shorter term storage in humid conditions (e.g., 75% RH or higher). The values obtained therefore demonstrate that the formulations of Batch 1 and Batch 2 (or other equivalent batches produced in the same way using ethanol 96.5% w/w) can be used to demonstrate the effect of inclusion of DCSG within a formulation of fluticasone/formoterol on the parameters listed within Table 6, above, as would be found, for example, after long-term storage of the formulation.

It can be seen that the drug concentration for the formulation with DCSG was higher than that of Batch 2 with 95.1% of target fluticasone and 95.5% of target formoterol content achieved with DCSG in comparison to 92.2% and 90.6% respectively without DCSG. This could be associated with drug losses during manufacturing due to drug absorption on the manufacturing equipment.

TABLE 8

Dose content uniformity (inter-inhaler) of Fluticasone/formoterol formulation 100/10 batches 1 (Fluticasone/formoterol formulation 100/10 with DSCG) and 2 (without DSCG) upon release from the MDI.

|  | Batch No. | |
| --- | --- | --- |
|  | 1 | 2 |
| Mean delivered dose of fluticasone [μg] (RSD %, n = 10) | 92.0 (5.2%) | 79.0 (4.7%) |
| Mean delivered dose of formoterol [μg] (RSD %, n = 10) | 8.9 (6.0%) | 7.4 (4.8%) |

Table 8 shows the results of testing dose delivery from 10 inhalers for each Batch. The inclusion of DCSG within the formulation is shown to deliver a higher dose of both drugs (e.g. 92% with DCSG in comparison to 79% without for fluticasone).

TABLE 9

Dose content uniformity through canister life of Fluticasone/formoterol formulation 100/10 batches 1 (Fluticasone/formoterol formulation 100/10 with DSCG) and 2 (without DSCG) upon release from the MDI.

|  | Batch No. | |
| --- | --- | --- |
|  | 1 | 2 |
| Mean delivered dose of fluticasone [μg] (RSD %, n = 9) | 89.6 (8.0%) | 79.9 (3.8%) |
| Mean delivered dose of formoterol [μg] (RSD %, n = 9) | 8.8 (7.7%) | 7.5 (5.5%) |

The results of the dose content uniformity study during the life of the canister, as shown in Table 9, also shows that a higher dose of both drugs is delivered by Batch 1 (with DCSG) (89.6% with DCSG in comparison to 79.9% without for fluticasone).

TABLE 10

Drug and DSCG residue in canister and on valve after exhaustion of Fluticasone/formoterol formulation 100/10 batches 1 (Fluticasone/formoterol formulation 100/10 with DSCG) and 2 (without DSCG) upon release from the MDI.

|  | Can | Valve | Total |
| --- | --- | --- | --- |
| Batch 1 |  |  |  |
| Formoterol assay [μg] (RSD %, n = 3) | 31.2 (13.4%) | 31.9 (21.3%) | 63.1 (13.8%) |
| Fluticasone assay [μg] (RSD %, n = 3) | 330 (14.7%) | 278 (22.3%) | 608 (13.5%) |
| DSCG assay [μg] (RSD %, n = 3) | 74.8 (16.9%) | 69.4 (23.0%) | 144 (15.1%) |
| Batch 2 |  |  |  |
| Formoterol assay [μg] (RSD %, n = 3) | 51.4 (17.2%) | 62.7 (14.0%) | 114.1 (15.1%) |
| Fluticasone assay [μg] (RSD %, n = 3) | 539 (16.5%) | 561 (16.7%) | 1100 (15.8%) |
| DSCG assay [μg] (RSD %, n = 3) | N.A. | N.A. | N.A. |

The above table shows that nearly twice as much of both drugs was recovered from canisters and valve of Batch 2 in comparison to Batch 1 (with DCSG) (e.g. 608 μg of fluticasone recovered for Batch 1, compared with 1100 μg for Batch 2).

FIG. 1 shows the aerodynamic particle size distribution results of tests performed on five inhalers for each batch. Similar to the dose delivery results in Tables 4 and 5, less fluticasone and formoterol were delivered from the actuator for Batch 2 in comparison to Batch 1.

FIG. 2 shows the results of time-lapse photography for glass vials containing formulations of the two batches. The glass vials were also visually examined and the following differences in suspension stability were found.

Batch 1 (with DSCG) exhibited large loose floccules soon after cessation of agitation (this result was different from that seen when the formulation is not challenged with water) while Batch 2 (without DSCG) remained more disperse and more homogeneous.

After a longer period of time, however, Batch 1 remained in the loosely flocculated form, resulting in a bulky but readily redispersible sediment while Batch 2 appeared to form agglomerates of different densities, some of which sedimented and others of which floated. At least part of the sedimented material present within the glass vial of Batch 2, which formed a creamed material deposited on the glass vial surface at the liquid-gas interface, was difficult to redisperse into a homogeneous suspension.

Visual examination therefore revealed that Fluticasone/formoterol formulation with DSCG (Batch 1) floccules more rapidly than the same formulation when not challenged by additional water, but remained homogeneous long enough to provide a satisfactory and consistent dose uniformity. In contrast, the formulation without DSCG prepared for comparison (Batch 2) creamed rapidly and resulted in drug deposition on the glass vial surface at the liquid-gas interface. These visual observations therefore provide evidence that the formulation of the present invention is able to tolerate high amounts of internal water.

In conclusion, the use of DSCG as an enabling excipient in Fluticasone/formoterol formulation HFA-MDI thus provided a more robust finished drug product, particularly against moisture ingress, which occurs unavoidably during storage and use.

Example 3

The following batch was made up using the process described in Example 1:

TABLE 11

Batch 3 composition

| Composition | Description Batch 3 Fluticasone/formoterol formulation (nominal dose 250 µg fluticasone/ 12 µg formoterol) | |
|---|---|---|
| | % w/w | g |
| Fluticasone propionate | 0.1785 | 3.900 |
| Formoterol fumarate dihydrate | 0.0086 | 0.187 |
| Cromolyn sodium (DSCG) | 0.0343 | 0.749 |
| Ethanol | 1.43 | 31.2 |
| HFA 227 | qs to 100.0 | 2148.0 |

The filled unpouched inhalers were put into an investigational stability program for 6 months at 40° C./75% RH and Showed good product quality and robustness in the product performance tests, as shown by the results of Tables 12 and 13, below.

TABLE 12

Results of Andersen Cascade Impactor of fluticasone/formoterol formulation (250 µg fluticasone/12 µg formoterol) at release and after 1 to 6 months storage at 40° C./75% RH.

| Batch 3 | Release Mean (RSD %, n = 4) | 1 Month 40° C./75% RH | | 3 Months 40° C./75% RH | | 6 Months 40° C./75% RH | |
|---|---|---|---|---|---|---|---|
| | | Can 1 | Can 2 | Can 1 | Can 2 | Can 1 | Can 2 |
| Fluticasone | | | | | | | |
| Delivered dose [µg, 2 actuations] | 197 (7.2%) | 173.1 | 191.5 | 184.5 | 203.7 | 189.0 | 173.8 |
| Metered dose [µg, 2 actuations] | 211 (8.4%) | 198.5 | 207.2 | 204.7 | 216.6 | 229.5 | n.d. |
| Fine particle dose [µg, 2 actuations] | 102 (8.5%) | 79.7 | 83.7 | 80.0 | 86.0 | 102.7 | 73.4 |
| Fine particle fraction [% based on delivered dose] | 52.0 | 46.1 | 43.7 | 43.3 | 42.2 | 54.3 | 42.2 |
| Fine particle fraction [% based on metered dose] | 48.5 | 40.2 | 40.4 | 39.1 | 39.7 | 44.7 | n.d. |
| Formoterol | | | | | | | |
| Delivered dose [µg, 2 actuations] | 9.5 (5.1%) | 8.6 | 9.5 | 9.8 | 10.5 | 8.4 | 7.9 |
| Metered dose [µg, 2 actuations] | 10.9 (5.3%) | 11.5 | 11.3 | 12.7 | 12.5 | 10.5 | n.d. |
| Fine particle dose [µg, 2 actuations] | 5.6 (8.3%) | 5.3 | 5.7 | 5.6 | 6.0 | 5.4 | 3.8 |
| Fine particle fraction [% based on delivered dose] | 58.4 | 61.6 | 60.0 | 56.4 | 57.2 | 63.6 | 48.6 |
| Fine particle fraction [% based on metered dose] | 51.1 | 46.0 | 50.6 | 43.6 | 47.8 | 51.3 | n.d. |

TABLE 13

Results of delivered dose uniformity test through inhaler life of fluticasone/formoterol formulation (250 µg fluticasone/12 µg formoterol) at release and after 1 to 6 months storage at 40° C./75% RH.

| Batch 3 | Release N = 10 | 1 Month 40° C./ 75% RH N = 12 | 3 Months 40° C./ 75% RH N = 10 | 6 Months 40° C./ 75% RH N = 12 |
|---|---|---|---|---|
| Mean delivered fluticasone dose [µg/2 actuations] (RSD %) | 197 (3.7%) | 208 (4.0%) | 190 (11.7%) | 191 (5.9%) |
| Mean delivered formoterol dose [µg/2 actuations] (RSD %) | 10.2 (7.0%) | 10.4 (4.3%) | 9.3 (12.3%) | 9.2 (5.8%) |

Example 4

The following batches were made up using the process described in Example 1:

TABLE 14

Composition of Batch 4 and Batch 5.

| Composition | Batch 4 Fluticasone/formoterol formulation (nominal dose 500 μg fluticasone/20 μg formoterol) % w/w | Batch 5 Fluticasone/formoterol formulation (nominal dose 500 μg fluticasone/10 μg formoterol) % w/w |
|---|---|---|
| Fluticasone propionate | 0.3571 | 0.3571 |
| Formoterol fumarate dihydrate | 0.0143 | 0.0071 |
| DSCG | 0.0343 | 0.0343 |
| Ethanol | 1.43 | 1.43 |
| HFA 227 | qs to 100.0 | qs to 100.0 |

The results of the stability investigation up to 12 months demonstrated good product quality and robustness of both formulations, as shown by the results displayed in Tables 15 and 16, below.

TABLE 15

Summary of ACI results of fluticasone/formoterol formulation Flutiform 250/10 (Batch 4) up to 12 months at 25° C./60% RH and 40° C./75% RH. Each result is the mean of 6 determinations (beginning and end of 3 canisters).

| | 25° C./60% RH | | | | 40° C./75% RH | | | |
|---|---|---|---|---|---|---|---|---|
| | Initial | 3 months | 6 months | 12 months | 1 month | 3 months | 6 months | 12 months |
| Fluticasone | | | | | | | | |
| Metered dose [μg] | 428.9 419.8 | 426.8 427.7 | 425.9 454.8 | 429.3 437.1 | 412.6 442.3 | 449.8 430.0 | 431.2 447.9 | |
| Delivered dose [μg] | 407.5 400.9 | 407.3 413.9 | 408.5 434.2 | 413.5 417.0 | 392.2 423.2 | 417.3 415.6 | 414.1 429.8 | |
| FPD (St 3-F) [μg] | 173.6 184.0 | 179.1 181.8 | 184.0 186.1 | 177.0 180.1 | 177.0 193.2 | 183.1 174.7 | 181.0 172.1 | |
| Group 1 (MP-USP throat) [μg] | 186.2 172.6 | 185.2 179.5 | 180.3 195.9 | 182.6 185.6 | 164.9 179.9 | 206.5 182.6 | 179.6 196.6 | |
| Group 2 (St 0-St 2) [μg] | 60.2 52.3 | 52.6 56.7 | 53.5 65.0 | 60.8 60.7 | 61.3 59.7 | 52.5 63.3 | 61.5 69.9 | |
| Group 3 (St 3-St 5) [μg] | 168.8 178.5 | 174.2 177.1 | 179.2 181.1 | 172.1 175.1 | 172.4 188.6 | 178.1 170.7 | 176.6 168.5 | |
| Group 4 (St 6-F) [μg] | 4.9 5.5 | 5.0 4.7 | 4.8 5.0 | 4.8 5.0 | 4.6 4.7 | 5.0 3.9 | 4.4 3.7 | |
| Formoterol | | | | | | | | |
| Metered dose [μg] | 18.50 18.27 | 18.12 18.22 | 18.00 19.25 | 17.60 18.15 | 17.51 18.59 | 19.05 18.42 | 18.21 18.43 | |
| Delivered dose | 16.89 16.71 | 16.47 16.89 | 16.57 17.54 | 16.34 16.76 | 16.05 17.13 | 16.56 17.04 | 16.76 16.81 | |
| FPD (St 3-F) [μg] | 8.40 8.87 | 8.66 8.90 | 9.04 9.01 | 8.29 8.61 | 8.48 9.23 | 8.92 8.64 | 9.00 8.23 | |
| Group 1 (MP-USP throat) [μg] | 8.06 7.61 | 7.67 7.42 | 7.21 8.16 | 7.30 7.49 | 7.01 7.42 | 8.44 7.72 | 7.23 8.03 | |
| Group 2 (St 0-St 2) [μg] | 1.75 1.41 | 1.45 1.57 | 1.45 1.81 | 1.68 1.68 | 1.70 1.61 | 1.42 1.74 | 1.67 1.85 | |
| Group 3 (St 3-St 5) [μg] | 8.18 8.60 | 8.43 8.68 | 8.81 8.77 | 8.08 8.36 | 8.27 9.00 | 8.69 8.44 | 8.79 8.05 | |
| Group 4 (St 6-F) [μg] | 0.22 0.27 | 0.23 0.23 | 0.23 0.23 | 0.21 0.25 | 0.21 0.23 | 0.23 0.20 | 0.21 0.18 | |

TABLE 16

Summary of ACI results of fluticasone/formaterol formulation Flutiform 250/5 (Batch 5) up to 12 months at 25° C./60% RH and 40° C./75% RH. Each result is the mean of 6 determinations(beginning and end of 3 canisters).

|  | 25° C./60% RH | | | 40° C./75% RH | | | |
|---|---|---|---|---|---|---|---|
|  | Initial | 6 months | 12 months | 1 month | 6 months | 12 months |
| Fluticasone | | | | | | | |
| Metered dose [µg] | 402.2 | 432.1 | 426.9 | 433.0 | 420.3 | 419.0 | 417.1 | 431.4 | 428.9 | 417.9 |
| Delivered dose [µg] | 378.4 | 413.9 | 411.6 | 416.2 | 405.5 | 404.5 | 401.0 | 412.1 | 417.3 | 402.7 |
| FPD (St 3-F) [µg] | 181.0 | 203.2 | 195.1 | 193.6 | 185.6 | 185.0 | 181.2 | 194.1 | 193.9 | 178.9 |
| Group 1 (MP-USP throat) [µg] | 171.5 | 175.9 | 180.1 | 175.6 | 178.9 | 181.4 | 183.7 | 179.9 | 175.5 | 171.2 |
| Group 2 (St 0-St 2) [µg] | 42.1 | 46.3 | 46.2 | 54.2 | 47.8 | 43.6 | 45.0 | 50.8 | 52.3 | 58.1 |
| Group 3 (St 3-St 5) [µg] | 177.1 | 199.1 | 190.8 | 189.9 | 182.0 | 181.0 | 177.2 | 190.7 | 190.3 | 175.7 |
| Group 4 (St 6-F) [µg] | 3.8 | 4.0 | 4.4 | 3.7 | 3.6 | 4.0 | 4.0 | 3.4 | 3.5 | 3.2 |
| Formoterol | | | | | | | | | | |
| Metered dose [µg] | 8.47 | 9.28 | 9.22 | 9.22 | 8.78 | 9.09 | 9.10 | 9.13 | 9.07 | 8.49 |
| Delivered dose [µg] | 7.62 | 8.38 | 8.40 | 8.45 | 8.03 | 8.36 | 8.26 | 8.23 | 8.37 | 7.76 |
| FPD (St 3-F) [µg] | 3.81 | 4.42 | 4.28 | 4.27 | 4.04 | 4.08 | 4.00 | 4.19 | 4.20 | 3.82 |
| Group 1 (MP-USP throat) [µg] | 3.78 | 3.91 | 4.01 | 3.84 | 3.79 | 4.04 | 4.14 | 3.94 | 3.84 | 3.59 |
| Group 2 (St 0-St 2) [µg] | 0.75 | 0.82 | 0.81 | 0.92 | 0.81 | 0.79 | 0.81 | 0.86 | 0.89 | 0.92 |
| Group 3 (St 3-St 5) [µg] | 3.75 | 4.34 | 4.19 | 4.17 | 3.97 | 3.96 | 3.89 | 4.11 | 4.11 | 3.75 |
| Group 4 (St 6-F) [µg] | 0.06 | 0.08 | 0.10 | 0.10 | 0.08 | 0.11 | 0.11 | 0.08 | 0.09 | 0.07 |

The invention claimed is:

1. A method for preparing a stabilized medicinal aerosol suspension formulation of micronized formoterol fumarate dihydrate (FFDH) and micronized fluticasone propionate (FP) in a liquid phase comprising an HFA propellant, or pharmaceutically acceptable salts thereof, for MDI administration, the method comprising selecting amounts of (a) FFDH and (b) FP to achieve the required therapeutic dose, measuring the true particle density of (a), (b) and (c), a moisture-scavenger excipient comprising sodium cromolyn, by a method comprising helium pycnometry, determining the density of the liquid phase, calculating the required amount of (c) needed to form floccules of (a), (b), and (c) having an average density the same as the density of the liquid phase ±0.2 g/cm$^3$, incorporating the selected amounts of (a), (b), and the calculated amount of (c) into the liquid phase, and forming floccules of (a), (b), and (c) having a density substantially the same as that of the liquid phase and providing a stabilized medicinal aerosol suspension formulation of FFDH and FP for MDI administration, wherein the amounts of (a), (b), and (c), are based on the total weight of the formulation and are selected from within the following ranges a) 0.003-0.04%;
b) 0.01-0.6%;
c) 0.01-0.1%;

the HFA propellant is HFA 227, and the formulation has stability over a storage period from 3 to 18 months and the water content of the formulation after the storage period is in the range of 500 ppm to 800 ppm.

2. The method of claim 1, wherein the average density of the floccules is the same as the density of the propellant, ±0.1 g/cm$^3$ or ±0.05 g/cm$^3$.

3. The method of claim 1, wherein the amount of (a) is 0.004-0.03% w/w or 0.005-0.02% w/w.

4. The method of claim 1, wherein the amount of (a) is 0.0071% w/w.

5. The method of claim 1, wherein the amount of (b) is 0.02-0.5% w/w.

6. The method of claim 1, wherein the amount of (b) is 0.03-0.4% w/w.

7. The method of claim 1, wherein the pharmaceutical suspension formulation further comprises a wetting agent.

8. The method of claim 7, wherein the wetting agent is a dehydrated alcohol.

9. The method of claim 8, wherein the dehydrated alcohol is ethanol.

10. The method of claim 9, wherein the dehydrated alcohol is present in an amount of from 0.01 to 3% by weight.

11. The method of claim 9, wherein the dehydrated alcohol is present in an amount of from 0.05 to 2.5% by weight.

12. The method of claim 9, wherein the dehydrated alcohol is present in an amount of from 1 to 2% by weight.

13. The method of claim 1, wherein the amount of (c) is 0.03-0.04% w/w.

* * * * *